United States Patent [19]

McClure

[11] Patent Number: 4,533,745

[45] Date of Patent: Aug. 6, 1985

[54] AMINO KETONES AND THEIR PREPARATION

[75] Inventor: David E. McClure, Lansdale, Pa.

[73] Assignee: Merck & Co., inc., Rahway, N.J.

[21] Appl. No.: 213,980

[22] Filed: Dec. 8, 1980

[51] Int. Cl.$^3$ ............................................ C07C 105/06
[52] U.S. Cl. ........................................ 560/28; 560/24; 560/27; 560/29; 560/30; 564/428; 564/393; 564/302
[58] Field of Search .............................. 560/28, 27, 24

[56] References Cited

U.S. PATENT DOCUMENTS

| | | | |
|---|---|---|---|
| 3,359,300 | 12/1967 | Skorcz | 560/28 |
| 3,634,490 | 1/1972 | Carr et al. | 560/24 |
| 3,940,434 | 2/1976 | Haas et al. | 560/28 X |

FOREIGN PATENT DOCUMENTS 2225247  7/1972  Fed. Rep. of Germany ........ 560/24

OTHER PUBLICATIONS

E. Dornberger, Liebigs Ann. Chem. 743, 42-49 (1971).
N. Levin et al., J. Org. Chem. 9, 380-391 (1944).
R. V. Heinzelmann et al., J. Org. Chem. 14, 907-910.
Remik et al., Lieb. Ann. Chem. 725, 116 (1969).

*Primary Examiner*—Charles F. Warren
*Attorney, Agent, or Firm*—Gabriel Lopez; Daniel T. Szura; Hesna J. Pfeiffer

[57] ABSTRACT

Amino ketone enantiomers and their direct preparation are disclosed. The ketone may be reduced to yield carbinol enantiomer which has pharmaceutical activity.

2 Claims, No Drawings

AMINO KETONES AND THEIR PREPARATION

BACKGROUND OF THE INVENTION

The present invention concerns amino ketone enantiomers and their direct preparation from an enantiomeric precursor using Friedel Crafts catalysis.

Aminoindanols of the formula:

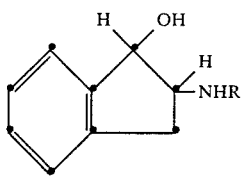

A where R is H or $CH_3$ are disclosed in the literature [(see e.g. E. Dornberger, Liebigs Ann. Chem. 743, 42–49 (1971); N. Levin et al., J. Org. Chem. 9, 380–391; R. V. Heinzelmann et al., J. Org. Chem. 14, 907–910; Remik et al., Lieb. Ann. Chem. 725, 116 (1969)]. The formula A compounds have two chiral centers at the 1 and 2 positions. Thus, four enantiomers, comprising two pairs, are possible. The enantiomeric pairs are designated as cis and trans. The Formula A compounds and their enantiomers are indicated to have pharmaceutical activity like ephedrine e.g. as bronchodilators.

Preparation of the A compounds is generally carried out by catalytic reduction of the corresponding ketone of the formula:

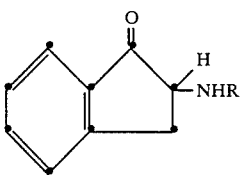

B which yields a mixture of enantiomers. A process has been discovered for direct preparation of a single enantiomer of Formula B which is then converted directly to a single enantiomer of Formula A.

SUMMARY OF THE INVENTION

A process for preparing an enantiomer of an aminoindanol by (1) preparing an enantiomer of an aminoindanone or phenylketone via Friedel Crafts reaction of an $N-CO_2R$ protected amino acid enantiomer and (2) subsequently reducing the product from (1); the intermediate from (1); and the (1) process step.

DESCRIPTION OF THE PREFERRED EMBODIMENTS

An embodiment of the present invention is a process for preparing an enantiomer of a compound of the formula

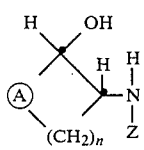

I wherein Z is H or $CH_3$ wherein (A) is a phenyl or substituted phenyl group and n is 1–3 which comprises, (1) when Z is $CH_3$,
(i) the reaction of an enantiomer of a compound of the formula

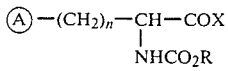

II wherein X is Cl, Br or OH and R is $C_1$–$C_6$ alkyl with a Friedel Crafts catalyst to produce a corresponding enantiomer of a compound of the formula

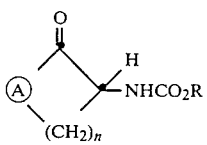

III (ii) reducing the formula III compound to obtain the formula I compound wherein Z is $CH_3$ and (2) when Z is H, additionally hydrolyzing the product from (ii) to obtain the formula I wherein Z is H. An intermediate reduction product obtained in step (2) has the formula

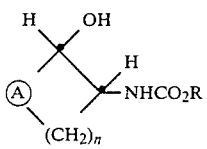

By corresponding enantiomer we mean that the optical configuration at the amino center in III has been established and is identical to that present in II.

The four enantiomers of the Formula I or III compounds are designated as 1S, 2S; 1R, 2S, 1R, 2R and 1S, 2R. The isomer pairs 1S, 2R and 1R, 2S are designated cis; the 1S, 2S and 1R, 2R pairs are designated trans.

(A) is phenyl or substituted phenyl group. The substituted phenyl group may have 1 or 2 substituents selected from $OCH_3$ and OH. Examples of substituted phenyl groups are

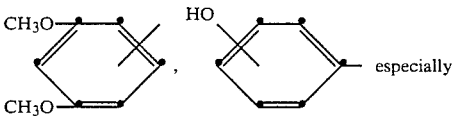

especially

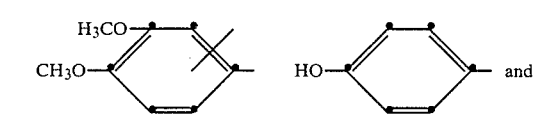

and

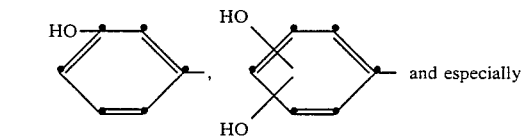

and especially

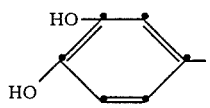

and the like.

Any Friedel Crafts catalyst may be used such as $BF_3$, $FeCl_3$, $AlBr_3$, with the aluminum halides being preferred but $AlCl_3$ being most preferred. Where R=OH, Polyphosphoric acid (PPA), and related catalysts may be used to give the required intermediate acylium ion.

Reduction may be carried out using any convenient reducing agent system. Thus, reduction may be carried out with $LiAlH_4$ (LAH), or other metallo organic hydride; with $H_2$ and catalyst e.g. $Pd/H_2$, with $BH_3 \cdot THF$ followed by $LiAlH_4$ and the like.

Reduction with a hydride reagent yields the trans isomers substantially free of the cis. Catalytic reduction yields a mixture of cis and trans isomer which can be separated by conventional methods. R is $C_1$–$C_6$ alkyl such as $CH_3$, n-hexyl, $-C(CH_3)_3$, ethyl and the like.

A flow sheet illustrating the process follows

FLOW SHEET

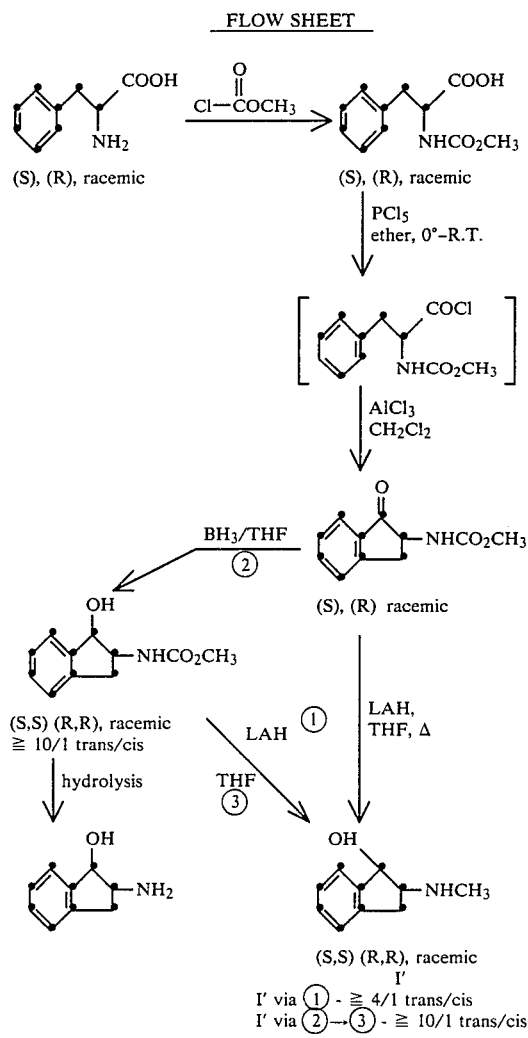

I' via ①  - ≧ 4/1 trans/cis
I' via ②→③ - ≧ 10/1 trans/cis

The formula I compounds have pharmaceutical utility like epinephrine e.g. as bronchodilators, or adrenergic agents.

Another embodiment of this invention is the step (1) process described above and the formula II intermediate therefrom.

Another embodiment of the present invention is a process for preparing a compound of the formula

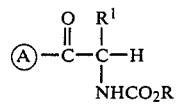

wherein R is $C_1$–$C_6$ alkyl A is phenyl or substituted phenyl and $R^1$ is H or $C_1$–$C_6$ alkyl especially $CH_3$ which comprises coupling of a compound of the formula

with a compound of the formula

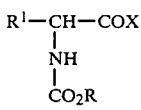

where X is Cl, Br or OH in the presence of a Friedel Crafts catalyst.

When $R^1$ in formula VI is other than H, there is a chiral center at the 2 carbon atom and the compound is optically active. Using an enantiomer of this compound where $R^1$ is e.g. $CH_3$ in the aforesaid reaction, an enantiomer of the formula IV compound will be obtained. The optical isomers are designated using conventional symbols such as (−) and (+), D and L, or d and L. The (S) and (R) designations which indicate fixed structural configuration are also used.

The formula IV compound be it racemic or enantiomeric may be reduced to yield (as illustrated by the following equation) the corresponding alkanolamines which have pharmaceutical activity. Reduction would yield a mixture of diastereomers which are subject to separation by conventional techniques. Thus, the use of a pure enantionmer of VI would yield an enantiomer of IV which upon reduction would produce two pure enantiomers diastereomeric to one another which may be separated.

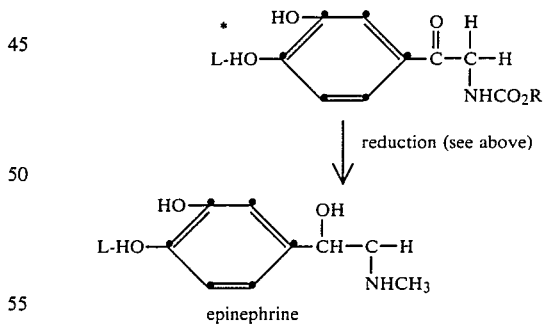

The following examples illustrate processes of the present invention.

EXAMPLE 1

(S)-2-Methoxycarbonylamino-1-indanone (2)

To an ice-cooled solution of L-phenylalanine (16.5 g., 0.1 m) in 1N NaOH (100 ml) to which solid $Na_2CO_3$ (5.3 g, 0.05 m) had been added was added to the methyl chloroformate (7.8 ml, 0.1 m). Stirring was continued for ½ hr. with cooling and ½ hr. without. The mixture was carefully acidified with concentrated HCl to pH 2-3. After extraction with CH$_2$Cl$_2$ and drying (Na$_2$SO$_4$), evaporation of the solvent left (S)-N-methoxycarbonylphenylalanine (1) (21 g, 94%)

To an ice-cooled solution of 1 in ether (300 ml) was added solid PCl$_5$ (19.4 g, 0.093 m). Stirring was continued for 1 hr. with cooling and ½ hr. without. After concentration of the mixture at 30° C./25 tarr, the residue was dissolved in CH$_2$Cl$_2$ (250 ml) and added dropwise rapidly to a suspension of AlCl$_3$ (37.2 g, 0.28 m, 3 m equiv.) in CH$_2$Cl$_2$ (150 ml). Stirring was continued for 1-2 hr after the addition had been completed. The mixture was poured into ice-cold, dilute HCl with vigorous stirring which was continued for 1 hr. The layers were separated and the aqueous phase was extracted several times with CH$_2$Cl$_2$. The combined organic phase was dried (Na$_2$SO$_4$), filtered through silica gel, and concentrated to give the product 2 (13.2 g, 64% overall); m.p. 157°-159°. A small portion of 2 was recrystallized from toluene; m.p. 164°-166° C.; $[E]_D^{25} + 134.1° (c=0.51, CHCl_3)$;

Analysis: Calculated for C$_{11}$H$_{11}$NO$_3$; 64.38% C; 5.40% H; 6.83% N. Found: 64.33% C; 5.50% H; 6.86% N.

EXAMPLE 2

(R)-2-Methoxycarbonylamino-1-indanone-(3)

Using the same procedure as in Example 1, but replacing L-phenylalanine with D-phenylalanine, the 3 compound [m.p. 162°-163° C.; $[\alpha]_D^{25} - 132.05° (C=0.44, CHCl_3)$] was obtained.

Analysis: Calculated: as above. Found: 64.21% C; 5.45% H; 6.91% N.

EXAMPLE 3

Racemic-2-Methoxycarbonylamino-1-indanone (4)

Using the same procedure as in Example 1, with racemic phenylalanine in place of L-phenylalanine, the 4 compound [m.p. 141°-143° C.] was obtained.

Analysis: Calculated: as above. Found: 64.79% C; 5.42% H; 6.82% N.

EXAMPLE 4

(1S, 2S)-2-Methylamino-1-indanol(5)

To lithium aluminum hydride (3.20 g, 0.085 m) in THF (100 ml) was added a suspension of (S)-N-methoxycarbonylamino-1-indanone 2 (8.72 g, 0.0425 m) in THF (100 ml) dropwise over ½ hr. The mixture was refluxed for ½ hr. and then cooled. A saturated aqueous Na$_2$SO$_4$ solution was added dropwise to quench the excess LAH. After stirring for ½ hr., CH$_2$Cl$_2$ was added along with solid Na$_2$SO$_4$ for drying, and the mixture was filtered. Evaporation of the solvent gave the crude product 5 which exhibited the following properties after trituration with hot butyl chloride; m.p. 140°-142° C; $[@]_D^{25} + 39.34 (C=0.516, CH_3OH)$.

Analysis: Calculated for C$_{10}$H$_{13}$NO; 73.57% C; 8.03% H; 8.59% N Found: 73.29% C; 8.04% H; 8.58% N.

EXAMPLE 5

(S)-2-Methoxycarbonylamino-1-phenylpropanone (7)

To an ice-cooled solution of L-alanine (17.8 g, 0.2 m) in 1N, NaOH (200 ml) to which solid Na$_2$CO$_3$ (10.6 g, 0.1 m) had been added was added methyl chloroformate (15.5 ml, 0.2 m). Stirring was continued for ½ hr. with cooling and ½ hr. without. The mixture was carefully acidified with conc. HCl to pH 2-3. After extraction with CH$_2$CL$_2$ and drying (Na$_2$SO$_4$), concentration of the solvent left (S)-N-methoxycarbonylalamine (6) (4.85 g, 16.5%).

To an ice-cooled solution of 6 in ether (100 ml) was added solid PCl$_5$ (6.86 g, 0.033 m). Stirring was continued for ½ hr. with cooling and ½ hr. without. After concentration of the mixture at 30°/25 tarr, the residue was dissolved in CH$_2$Cl$_2$ (20 ml). Stirring was continued for 1-2 hr. after the addition had been completed. The mixture was poured carefully into ice cold dilute HCl with vigourous stirring which was continued for ½ hr. The layers were separated and the aqueous phase was extracted once more with CH$_2$Cl$_2$. The combined organic phase was dried (Na$_2$SO$_4$), filtered through silica gel, and concentrated. Flash chromatography of the residue on Silica gel 60 (230-400 mesh) eluting with 5% CH$_3$OH/CH$_2$Cl$_2$ provided the product 7 as a yellow oil (3.6 g, 52.7%); $[@]_D^{25} - 10.4° (C=0.69, CHCl_3)$. A high resolution mass spectrum was consistent with the proposed structure as was the proton NMR spectrum. Chiral Shift NMR analysis indicated the presence of only 2-3% of the (R)-isomer.

EXAMPLE 6

Racemic-2-Methoxycarbonylamino-1-phenylpropane (8)

Using the same procedure as in Example 5, with racemic alamine in place of L-alanine, the 8 compound [yield=58%] was obtained. A high resolution mass spectrum was consistent with the proposed structure as was the proton NMR spectrum.

EXAMPLE 7

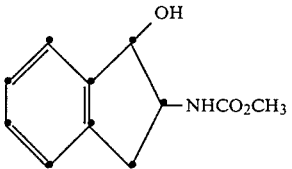

(1S, 2S)-2-N-Methoxycarbonylamino-1-indanol (9)

To a suspension of (S)-2-N-methoxycarbonylamino-1-indanone (2.05 g. 0.01 m) in THF (25 ml) was added dropwise a solution of borane in THF (1 m, 10 ml, 0.01 m) while cooling in an ice bath. Stirring was continued for 2 hours while the mixture warmed to room temperature. Acetic acid and methanol were carefully added, and the mixture was concentrated on a rotary evaporator. The residue was again treated with methanol and reconcentrated. After pumping on to remove residual solvent, the 9 compound was isolated (1.95 g, 94%). Recrystallization from CHCl$_3$ gave 9; mp 176°-178° C; $[\alpha]_D^{25} 23.62° (C=0.58, CH_3OH)$.

EXAMPLE 8

Racemic-2-N-Methoxycarbonylamino-1-indanol (10)

The substitution of racemic 2-N-methoxycarbonylamino-1-indanone for the (S)-isomer in the Example 7 procedure led to the formation of racemic compound 10, m.p.—178°-180° C.

EXAMPLE 9

(1S, 2S)-2-methylamino-1-indanol (5)

The substitution of (1S, 2S)-9 for the starting material [(S)-2] in Example 4 led to the formation of 5 having identical properties to those shown in Example 4.

EXAMPLE 10

(1S, 2S)-2-amino-1-indanol (11)

To triethylamine (1.3 g, 0.013 m) and (1S, 2S)-2-N-methoxycarbonylamino-1-indanol (9), (1.03 g, 0.05 m) in THF (50 ml) was added trichlorosilane (1.20 ml, 0.012 m) via syringe. The mixture was refluxed 4 hr. and then cooled. The mixture was partially concentrated on a rotary evaporator prior to the addition of 25 ml 2N HCl, and then heating on a steam bath was conducted for 15–30 min. After cooling, the mixture was extracted with ether. The aqueous phase was basified with aqueous NaOH and then extracted with ethyl acetate. After drying and concentration, the desired product (11) was obtained. The HCl salt of 11 was formed in ethanol/ether and recrystallized from the same solvent; m.p. 207°–209°; $[\alpha]_D^{25}$ 15.56°(C=0.54, $H_2O$) [lit. for the (R,R)-isomer; m.p. 206°–209°; $[\alpha]_D^{25}$ −13.4°(C=0.75, $H_2O$).

Claims to the invention follow.

What is claimed is:

1. A compound having the formula

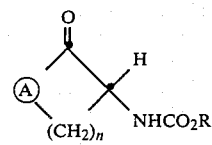

wherein A is phenyl or substituted phenyl group, n is 1–3 and R is $C_1$–$C_6$ alkyl.

2. The compound of claim 1 wherein R is $CH_3$.

* * * * *